(12) United States Patent
Gao

(10) Patent No.: US 8,624,200 B2
(45) Date of Patent: Jan. 7, 2014

(54) OPTICAL DETECTION SYSTEM

(75) Inventor: Songping Gao, Ashland, MA (US)

(73) Assignee: Analogic Corporation, Peabody, MA (US)

( * ) Notice: Subject to any disclaimer, the term of this patent is extended or adjusted under 35 U.S.C. 154(b) by 275 days.

(21) Appl. No.: 13/154,710

(22) Filed: Jun. 7, 2011

(65) Prior Publication Data

US 2012/0313009 A1    Dec. 13, 2012

(51) Int. Cl.
*G01N 21/03* (2006.01)
*G01N 21/65* (2006.01)

(52) U.S. Cl.
USPC .................. 250/458.1; 356/301; 356/317

(58) Field of Classification Search
USPC ............... 250/458.1–461.2; 356/301, 417
See application file for complete search history.

(56) References Cited

U.S. PATENT DOCUMENTS

| | | | | |
|---|---|---|---|---|
| 5,469,264 A | * | 11/1995 | Shigemori | 356/417 |
| 5,538,691 A | * | 7/1996 | Tosa et al. | 356/246 |
| 5,922,285 A | * | 7/1999 | Melendez et al. | 422/82.08 |
| 7,300,800 B2 | * | 11/2007 | Bell et al. | 436/172 |
| 2005/0110990 A1 | * | 5/2005 | Koo et al. | 356/301 |
| 2009/0097022 A1 | * | 4/2009 | Shen et al. | 356/301 |

* cited by examiner

*Primary Examiner* — Casey Bryant
(74) *Attorney, Agent, or Firm* — Driggs, Hogg, Daugherty, Del Zoppo Co., LPA

(57) ABSTRACT

An optical detection system includes a sample carrier receiving region that receives a sample carrier carrying a sample. The system further includes a source that emits an excitation signal having a wavelength within a predetermined wavelength range. The excitation signal illuminates the sample carrier. A first sub-portion of the excitation signal is absorbed by the sample, which emits characteristic radiation in response thereto. A second sub-portion of the excitation signal traverses the sample carrier. The system further includes a detector that detects the characteristic radiation. The system further includes an absorber that absorbs the excitation signal traversing the sample carrier without being absorbed by the sample or sample carrier. The absorber absorbs at least 95% of the excitation signal traversing the sample carrier.

20 Claims, 10 Drawing Sheets

OPTICAL DETECTION SYSTEM

TECHNICAL FIELD

The following generally relates to an optical detection system and is described with a particular application to DNA analysis. However, the following is also amenable to other applications.

BACKGROUND

A micro-channel device includes one or more micro (sub-millimeter) channels through which one or more small volumes of samples are routed for processing and/or analysis. An example of such a device includes a sample carrier such as a biochip, a lab-on-a-chip, and/or other micro-channel device. An application in which a micro-channel device has been used is DNA sequencing. DNA sequencing generally is a method for determining an order of nucleotide bases (adenine, guanine, cytosine, and thymine) of DNA in a sample of DNA.

For DNA sequencing, the DNA in the sample is lysed, producing fragments of sequences of the four nucleotides. The fragments are replicated through polymerase chain reaction (PCR) and labeled with target specific fluorescent dyes (e.g., one for each nucleotide base), each dye having a different spectral emission characteristic (e.g., wavelength, frequency, energy and color). The labeled fragments are separated by size through electrophoresis. The DNA fragments are sequenced based on the spectral characteristics of the dyes.

Such sequencing has included using an optical detection system to illuminate the fragments with an excitation signal and detect fluoresced radiation from the dyes of the fragments. The detected spectral information is used to identify the nucleotides and sequence the DNA. However, only about five percent (5%) of the excitation signal is absorbed by the dyes; the other ninety-five percent (95%) traverses the sample carrier and can produce background signal, stray light, and noise inside the optical system, which may be detected along with the fluoresced radiation, which may negatively impact DNA sequencing.

One approach to mitigating the above includes placing a mirror behind the sample carrier to direct excitation signal traversing the sample carrier towards a "black box" collector, where the signal is collected and trapped. FIG. 1 shows an example in which a portion 102 of an excitation signal 104 traversing a sample carrier 106 is directed by a mirror 108 to a collector 110. Emission 112 represents signal emitted by a sample (carried by the sample carrier 106) in response to absorbing the excitation signal 104. Unfortunately, the mirror 108 and the collector 110 consume space. For example, in one instance, the mirror 108 and the collector 110 collectively occupy a volume on the order of about two inches by two inches by a half an inch (2"×2"×0.5"). Furthermore, the mirror 108 and the collector 110 increase overall system cost. At least in view of the foregoing, there is an unresolved need for other approaches for mitigating the excitation signal traversing the sample carrier without being absorbed.

SUMMARY

Aspects of the application address the above matters, and others.

In one aspect, an optical detection system includes a sample carrier receiving region that receives a sample carrier carrying a sample. The system further includes a source that emits an excitation signal having a wavelength within a predetermined wavelength range. The excitation signal illuminates the sample carrier. A first sub-portion of the excitation signal is absorbed by the sample, which emits characteristic radiation in response thereto. A second sub-portion of the excitation signal traverses the sample carrier. The system further includes a detector that detects the characteristic radiation. The system further includes an absorber that absorbs the excitation signal traversing the sample carrier without being absorbed by the sample or sample carrier. The absorber absorbs at least 95% of the excitation signal traversing the sample carrier.

In another aspect, a method includes illuminating a sample carrier with an excitation signal. The sample carrier carries a sample. A first sub-portion of the excitation signal is absorbed by the sample, which emits characteristic radiation in response thereto. A second sub-portion of the excitation signal traverses the sample carrier. The method further includes detecting, via a detector, the characteristic radiation. The method further includes absorbing via an absorber the excitation signal traversing the sample carrier. The absorber absorbs at least 95% of the excitation signal traversing the sample carrier.

In another aspect, a device configured to sequence DNA includes an optical detection system with a source that emits an excitation signal that illuminates a sample carrier carrying a plurality of DNA fragments labeled with amino acid specific fluorescent dyes, wherein a first sub-portion of the excitation signal is absorbed by the dyes, which emit characteristic radiation in response thereto, and a second sub-portion of the excitation signal traverses the sample carrier and an absorber that absorbs a portion of the excitation signal that traverses the sample carrier without being absorbed, wherein the absorber has a reflectance of less than a half a percent.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 2:
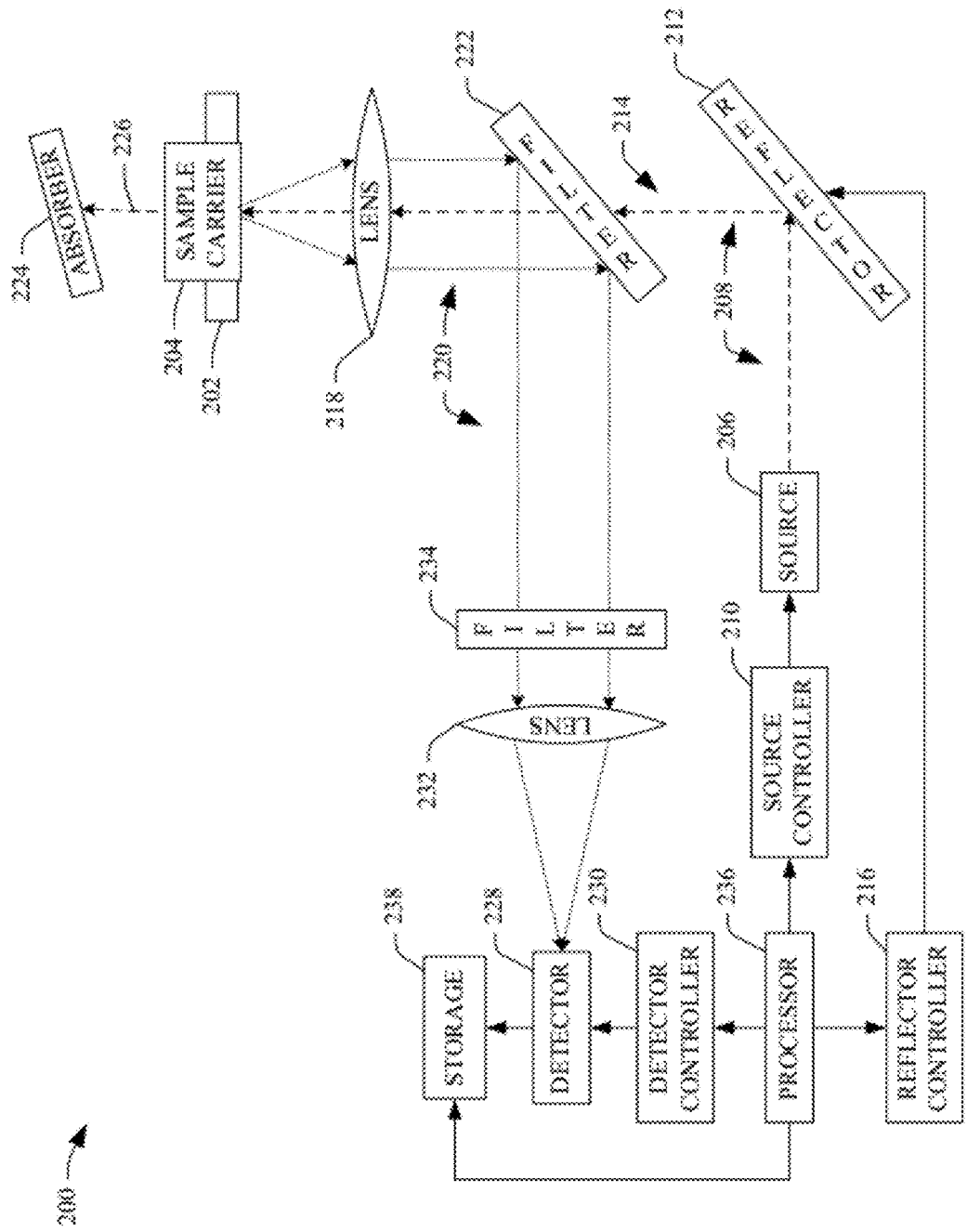
FIG. 2 schematically illustrates an example optical detection system including an absorber which removes excitation signal traversing a sample carrier in an optical detection system.

FIG. 2 illustrates an example optical detection system 200. The optical detection system 200 may be a stand alone system or part of another system such as a sample processor and/or analyzer, including, but not limited to, a DNA sequencer and/or other apparatus. The optical detection system 200 includes a sample carrier support region 202, which is configured to receive and support a sample carrier 204 for processing sample carried thereby. Examples of a suitable sample carrier include, but are not limited to, micro-channel devices such as a lab-on-a-chip (LOC), a biochip, micro-fluidic arrays, and/or other micro-channel devices and/or sample carriers.

The sample carrier 204 is configured to carry one or more samples for processing. A non-limiting example of a suitable sample includes a bio-sample such as one or more labeled DNA fragment and/or other sample. A suitable label includes a fluorescent or other material that absorbs an incident excitation signal (electromagnetic radiation) and emits a corresponding characteristic signal. In the context of DNA analysis, the label may include at least four different fluorescent dyes, each dye being target specific, binding to a different one of the four nucleotide bases (adenine (A), guanine (G), cytosine (C), and thymine (T)), and emitting or fluorescing characteristic radiation. One or more other dyes may also be included. For example, a calibration dye may also be included.

An electromagnetic radiation source (source) 206 generates and transmits an excitation signal 208 (electromagnetic radiation). An example of a suitable source 206 is a laser that transmits within a known electromagnetic radiation range (e.g., 488 nm, 532 nm, etc.). Other sources, including non-laser sources such as a light emitting diode (LED), an incandescent light, etc. are also contemplated herein. A source controller 210 controls the source 206, including activating the source 206 to transmit, adjusting the output power of the source 206, pulsing transmission, etc.

A beam reflector 212 such as a mirror or other reflector directs the transmitted signal 208 along a transmission path 214 from the reflector 212 to the sample carrier 204, for example, to a channel of the sample carrier 204 carrying a sample. The reflector 212 is movably mounted, and a reflector controller 216 is configured to controllably rotate, pivot or tilt the reflector 212 to scan or move the transmission path 214 across the sample carrier 204. In one non-limiting instance, the reflector 212 is mounted on an end of a rotary shaft and the controller 216 includes an electromagnetic device such as a closed loop Galvanometer that controllably deflects the shaft to move the reflector 212 and scan over the sample carrier 204.

A lens 218 is disposed between the sample carrier 204 and the reflector 212 in the transmission path 214 and is configured to focus the excitation signal 208 at the sample carrier 204. In the illustrated embodiment, the lens 218 focuses the excitation signal 208 such that it travels in a direction perpendicular towards the sample carrier 204. The lens 218 also collects fluorescent radiation emitted from the sample carrier 204 back along a signal collection path 220. The illustrated lens 218 includes a biconvex lens. However, other lenses such as a plano-convex or other lens that can suitably focus the excitation signal are also contemplated herein. Moreover, the lens 218 may include more than one lens. Furthermore, in another embodiment, the lens 218 is omitted.

A filter 222 is disposed between the lens 218 and the reflector 212 in the transmission and collection paths 214 and 220. The filter 222 is configured to filter radiation traversing the transmission path 212 such that substantially only excitation electromagnetic radiation having predetermined spectral characteristics of interest passes through the filter 222. The filter 222 is also configured to filter radiation traversing the collection path 220 such that substantially only electromagnetic radiation having predetermined spectral characteristics of interest is directed along the collection path 220. An example of a suitable filter includes a dichroic filter, band-pass filter, or other filter that selectively passes electromagnetic radiation based on spectral characteristics while reflecting other electromagnetic radiation based on spectral characteristics.

An absorber 224 includes a material that absorbs a portion 226 of the excitation signal 214 that traverses through the sample carrier 204 without being absorbed. As described in greater detail below, the absorber 224 is angularly oriented with respect to a direction of the excitation signal 226 traversing the sample carrier without being absorbed such that a predetermined amount (e.g., 90%, 95%, 99% or other percent) of the excitation signal 226 that traverses through the sample carrier 204 without being absorbed is absorbed by the absorber 224. In one instance, this allows for removing a substantial amount (e.g., 90%, 95%, 99%, etc.) of signal that might cause background, stray light, and/or noise in the optical detection system 200, mitigating the negative affects therefrom. Furthermore, in some embodiments, the absorber 224 requires less space and is less expensive than a configuration in which the system 200 includes a conventional mirror and black box collector.

A detector 228 is configured to detect electromagnetic radiation having spectral properties of interest and traversing the collection path 220 and to generate a signal indicative thereof. The detector 228 may include a photo-multiplier tube (PMT), a charge-coupled device (CCD) camera, or the like, and may be tunable or fixed. As described herein, the radiation characteristic of the sample carried by the sample carrier 204 is of interest and thus the detector 228 is configured to detect radiation having spectral properties corresponding to those of the sample carried by the sample carrier 204. In one embodiment, the detector 228 includes a plurality of sub-detectors, each configured to detect different bands of radiation within the range of interest. A detector controller 230 controls the detector 228. Such control includes, but is not limited to, adjusting the gain, activating and deactivating channels of the detector 228, etc.

A lens 232 is disposed between the filter 222 and the detector 228. The lens 232 focuses the radiation with respect to the detector 228. Similar to the lens 218, the lens 232 includes a biconvex lens, but alternatively can include other lenses such as a plano-convex or other lens that suitably focuses the radiation with respect to the detector 228. A filter 234 is disposed between the lens 232 and the filter 222. The filter 234 is configured to pass the radiation traversing the collection path and having predetermined spectral characteristics of interest and attenuate and/or reflect other electromagnetic radiation. In another embodiment, the filter 234 can be omitted. The collection path 220 is shown only for the particular scan location.

A processor 236 controls the detector controller 230, the source controller 210, and/or the reflector controller 216. The processor 236 and/or one or more processor local to the system 200, local to an apparatus including the system 200, and/or external and remote from the system may be configured to process detected signals, which can be stored in storage 238. In the context of processing samples, this may include sequencing DNA for DNA samples, and/or other processing.

Figure 3:
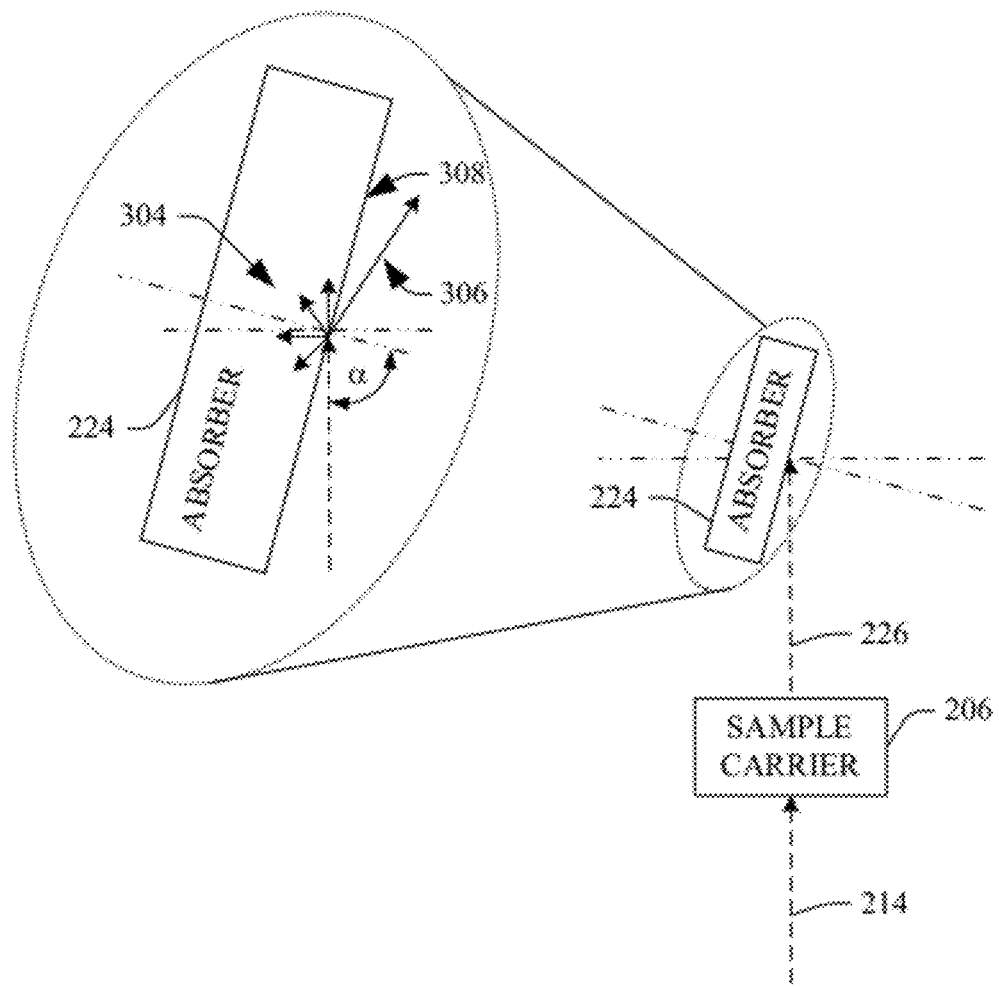
FIG. 3 schematically illustrates an example of the absorber.

FIG. 3 schematically illustrates an example of the absorber 224 in connection with the sample carrier 206 and the excitation radiation 226 traversing the sample carrier 206 without being absorbed by a sample carried by the sample carrier 206 for a particular excitation signal wavelength and absorber geometry. However, it is to be understood that this example is provided for explanatory purposes and is not limiting, and other excitation signal wavelengths and/or absorbers are contemplated herein.

In the illustrated embodiment, the source 206 (FIG. 2) includes a narrow beam (e.g., 10 to 100 micron diameter) 488 nanometer (±5 nm) 200 (~160) milliwatt laser. The excitation signal is linearly polarized and the polarization orientation is parallel to a plane of incidence of the absorber 224. The sample carrier 206 has length 300 of approximately 3.2 millimeters long and includes 16 channels, each configured to carry a sample. Sample carriers having other geometry and/or with more or less channels are also contemplated herein.

Figure 1:
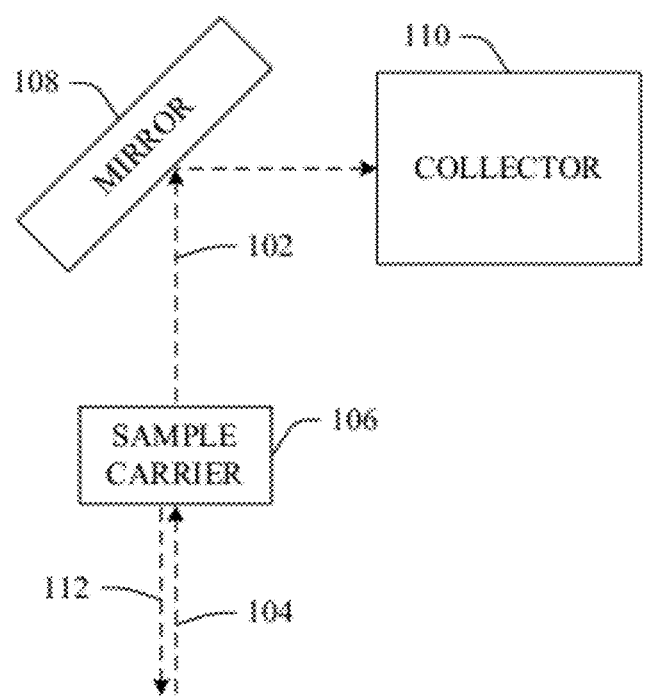
FIG. 1 schematically illustrates a prior art approach for removing excitation signal traversing a sample carrier in an optical detection system.

The illustrated absorber 224 includes silicon (Si) with a refraction (n) at 488 nm of: n=4.422+0.0163i, where 4.422 is the refraction index and 0.0163 corresponds to an absorption coefficient of silicon. A geometry of the illustrated absorber 224 is approximately 10 mm long by 20 mm wide by one millimeter thick (10×20×1 mm). Such geometry is substantially smaller than that of a conventional mirror and collector sub-system (FIG. 1). In other embodiments, the absorber 224 has other geometry. The illustrated absorber 224 can dissipate one or more watts of laser power.

In this example, the absorber 224 is oriented such that an angle α is about seventy-seven and four tenths (77.4) degrees. Note that the angle α is an angle between the excitation signal 226 and a normal to a surface 308 of incidence of the absorber 224. In this configuration, more than 99% of the excitation radiation 226 traversing the sample carrier without being absorbed by the sample is absorbed in the absorber 224 as shown at 304 and less then 1% of the excitation radiation portion 226 is reflected as shown at 306.

Various approaches can be utilized to determine cc. The following discusses a theoretical approach based on Maxwell's and Fresnel's equations. From these equations, when light moves from a medium of a given refractive index $n_1$ into a second medium with a given refractive index $n_2$, both reflection and refraction of the light may occur. The angles that the incident, reflected and refracted rays make to a normal of the interface between the media can be represented as $\theta_i$, $\theta_r$, and $\theta_t$, respectively. The relationship between these angles is given by the law of reflection: $\theta_i=\theta_r$; and Snell's law: $\sin(\theta_i)/\sin(\theta_t)=n_2/n_1$.

The fraction of the incident power that is reflected from the interface is given by the reflectance R and the fraction that is refracted is given by the transmittance T. For this example, the media are assumed to be non-magnetic. The calculations of R and T depend on polarization of the incident ray. If the light is polarized with the electric field of the light perpendicular to the plane of the incidence (s-polarized), the reflection coefficient R can be determined by Equations 1:

$$R_s = \left(\frac{n_1 \cos \theta_i - n_2 \cos \theta_t}{n_1 \cos \theta_i + n_2 \cos \theta_t}\right)^2 = \quad \text{Equation 1}$$

$$\left[\frac{n_1 \cos \theta_i - n_2 \sqrt{1-\left(\frac{n_1}{n_2}\sin \theta_i\right)^2}}{n_1 \cos \theta_i + n_2 \sqrt{1-\left(\frac{n_1}{n_2}\sin \theta_i\right)^2}}\right]^2,$$

wherein $\theta_t$ can be derived from $\theta_i$ by Snell's law and is simplified using trigonometric identities. If the incident light is polarized in the plane of the incidence (p-polarized), t the reflection coefficient R can be determined by Equation 2:

$$R_p = \left(\frac{n_1 \cos \theta_t - n_2 \cos \theta_i}{n_1 \cos \theta_t + n_2 \cos \theta_i}\right)^2 = \quad \text{Equation 2}$$

$$\left[\frac{n_1 \sqrt{1-\left(\frac{n_1}{n_2}\sin \theta_i\right)^2} - n_2 \cos \theta_i}{n_1 \sqrt{1-\left(\frac{n_1}{n_2}\sin \theta_i\right)^2} + n_2 \cos \theta_i}\right]^2.$$

For this example, the media are air (with a refraction index is n=1) and the silicon absorber 224 (with the complex refraction index of n=4.422+0.0163i, again, where 4.422 is refraction index and 0.0163 is the absorption coefficient of silicon at 488 nm).

Figure 4:
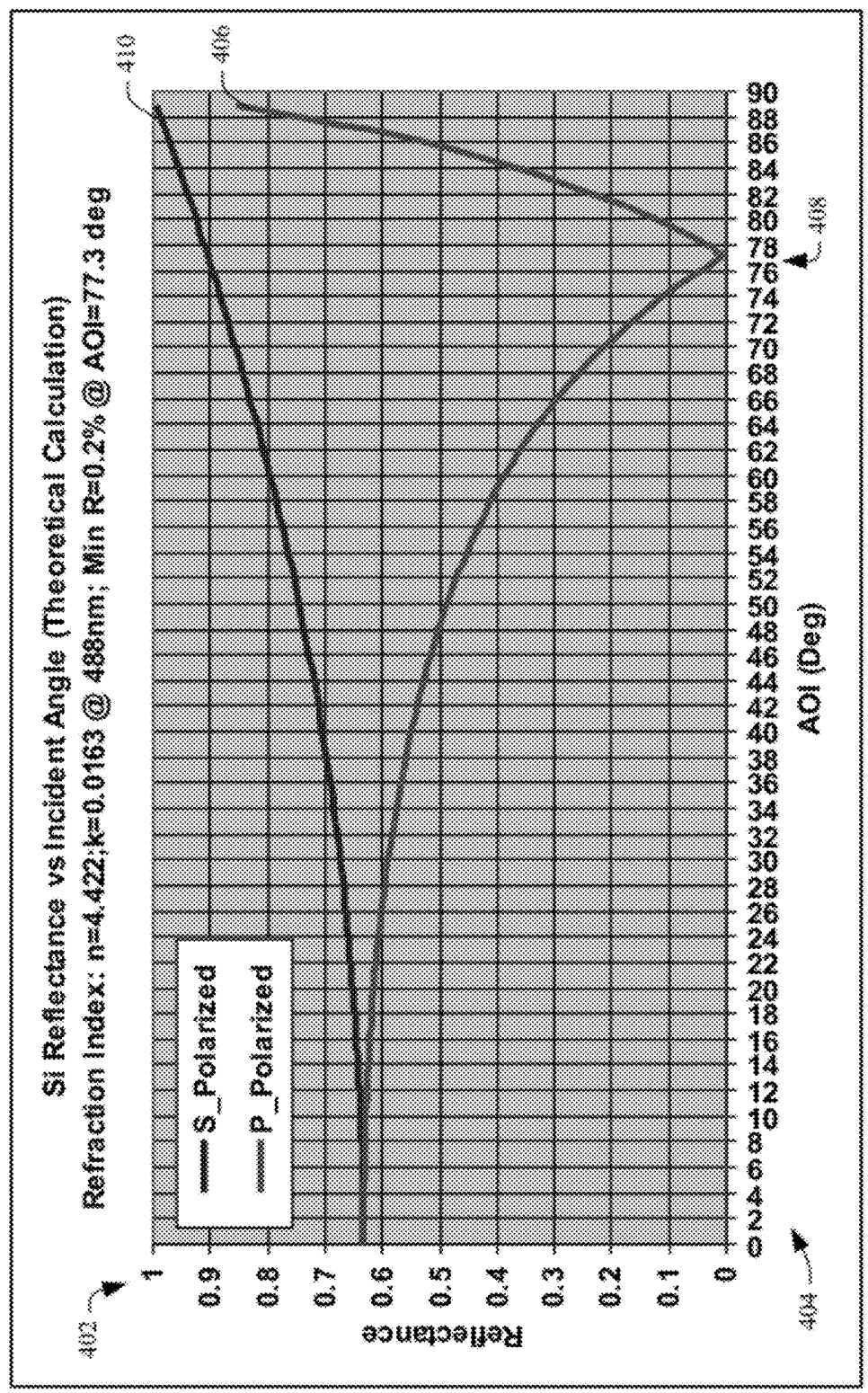
FIG. 4 illustrates a linear plot of reflectance as a function of incident angle for a silicon absorber illuminated with a 488 nm laser.
Figure 5:
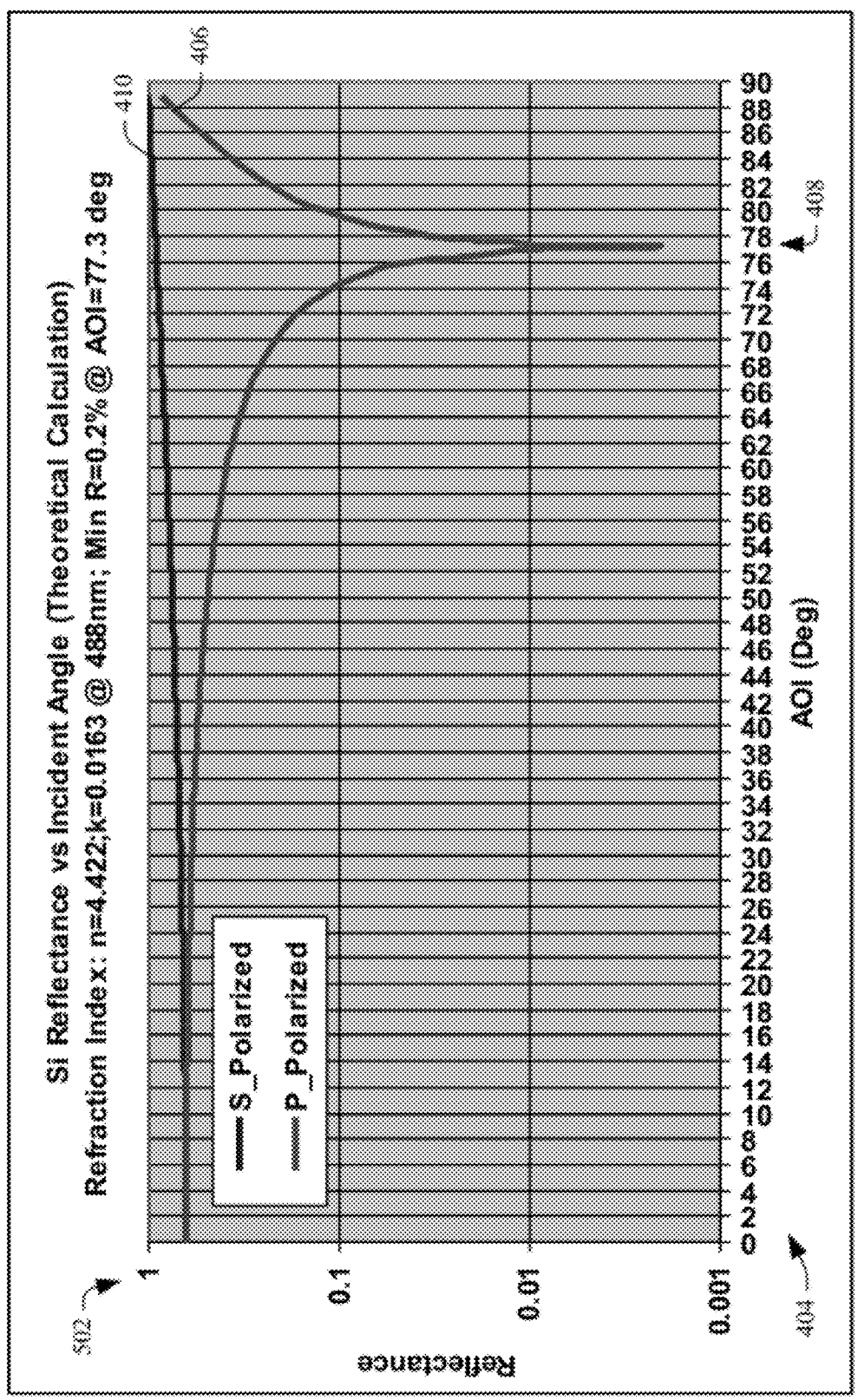
FIG. 5 illustrates a logarithmic plot of reflectance as a function of incident angle for a silicon absorber illuminated with a 488 nm laser.

The reflectance of 488 nm wavelength of light from the surface 308 varies with incident angle. An example of this is shown in FIG. 4, where a y-axis 402 represents reflectance and an x-axis 404 represents angle of incidence. In FIG. 4, a P-polarization component 406 has a minimal reflectance 408 of approximately 0.2%, at incident angle of approximately 77.4 degrees, and an S-polarization component 410 has a reflectance that increases with incident angle. FIG. 5 shows the same information, except that a y-axis 502 is represented in a logarithmic scale instead of a linear scale like the y-axis 402.

Variations are discussed.

Although FIGS. 3-5 show examples where the material of the absorber 224 is silicon, other materials are also contemplated herein. Suitable materials include, but are not limited to, materials with a minimal reflectance of less than five percent (5.0%) such as less than two percent (2.0%), less than one percent (1.0%), less than a half a percent (0.5%) or less than any other percent between zero (0.0%) and five percent (5.0%) for an angle α in an angular range from 0 to 90 degrees. The actual reflectance of various materials is determined by EQUATIONS 1 and 2.

Figure 6:
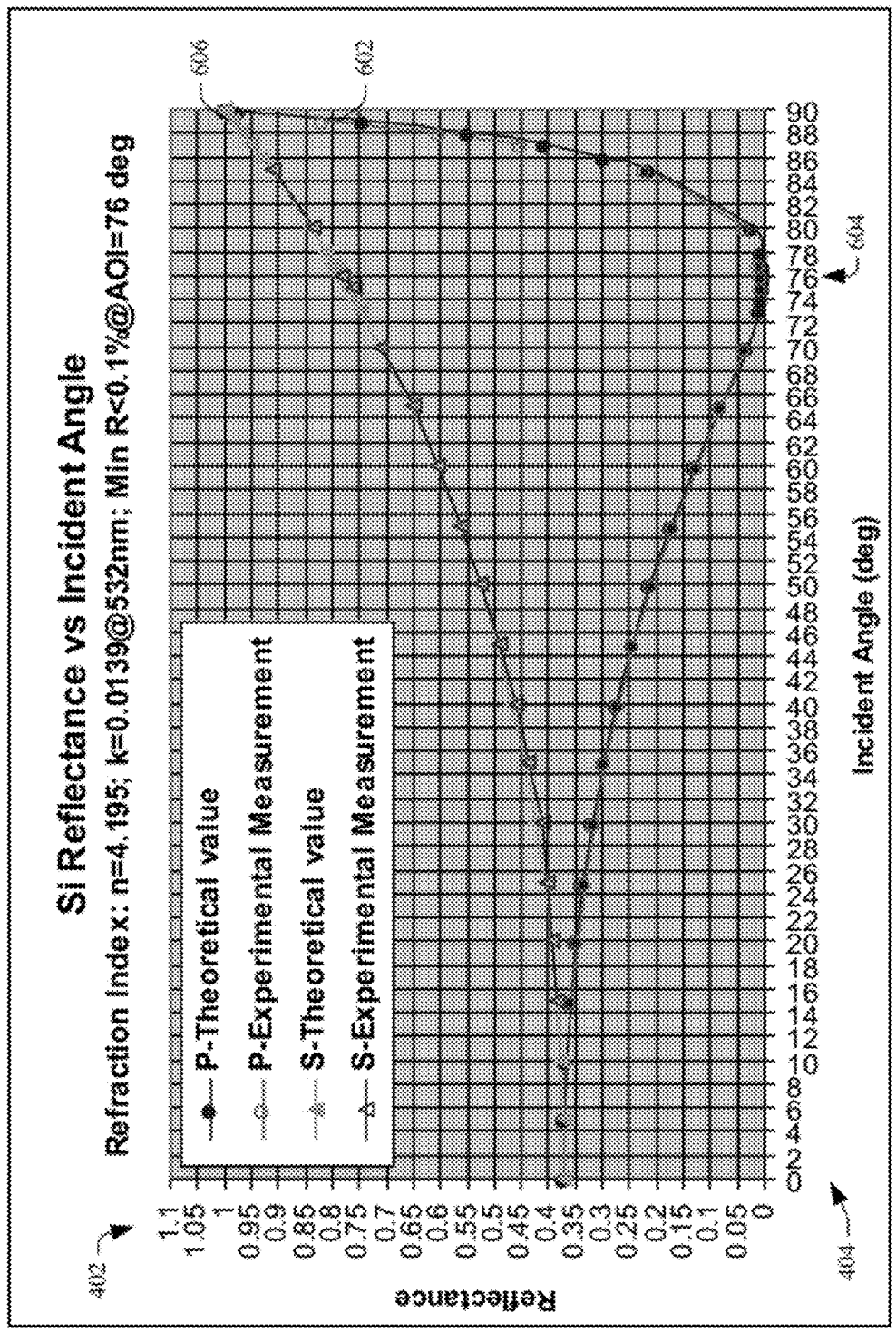
FIG. 6 illustrates a linear plot of reflectance as a function of incident angle for a silicon absorber illuminated with a 532 nm laser.
Figure 7:
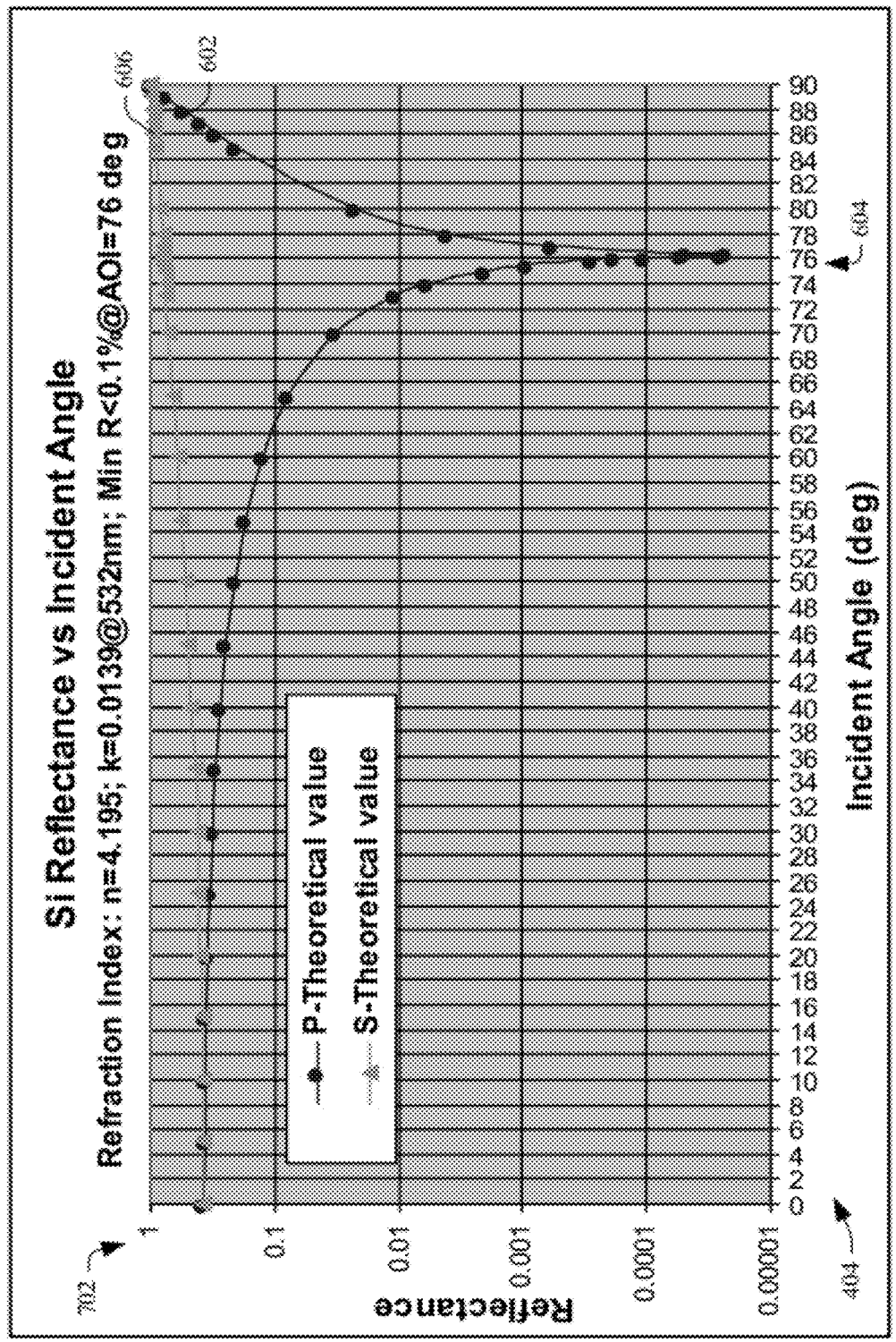
FIG. 7 illustrates a logarithmic plot of reflectance as a function of incident angle for a silicon absorber illuminated with a 532 nm laser.

In the above, the reflectance of a 488 nm wavelength of light from the silicon surface 308 is shown in FIGS. 4 and 5 as a function of incident angle. Equations 1 and 2 can also be utilized to determine the reflectance for other wavelengths. For example, FIG. 6 shows how reflectance of 532 nm light from the silicon surface. Here, a P-polarization component 602 has a minimal reflectance 604 of approximately 0.2% at incident angle of approximately 76.0 degrees, and an S-polarization component 606 reflectance increases with incident angle. FIG. 7 shows the same information, except that a y-axis 702 is represented in a logarithmic scale instead of a linear scale like the y-axis 602. Note that the angle at which minimal reflectance occurs shift s with laser wavelength (77.4 degrees for 488 nm (FIGS. 6 and 7), and 76.0 degrees fro 532 nm (FIGS. 4 and 5)).

In FIG. 3, the absorber 224 is angularly oriented in accordance with the minimal reflectance of approximately 77.4 degrees. However, the absorber 224 does not have to be orientated as such and can alternatively be angularly oriented from 0 to 90 degrees with respect to the axis. Thus, where the minimal reflectance is not achievable or not desired, another angle can be used.

Figure 8:
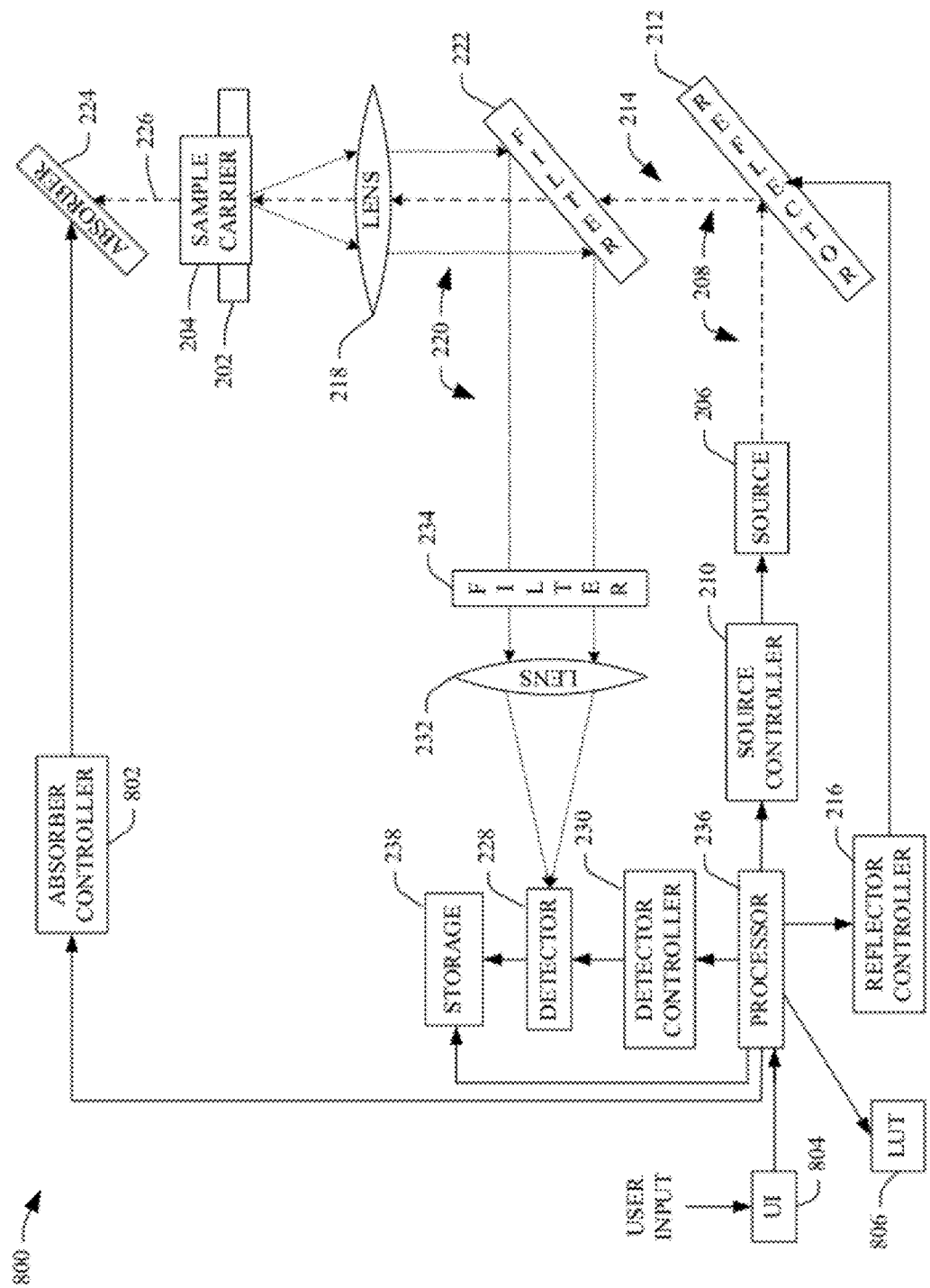
FIG. 8 schematically illustrates an example optical detection system configured to emit excitation signals having different wavelengths.

In FIG. 2, the system 200 is configured for a 488 nm laser and a silicon absorber 224. FIG. 8 shows a system 800, which is substantially similar to the system 200 of FIG. 2. However, in FIG. 8, the source 206 is controllable so that it can emit at one of a plurality different wavelengths and the absorber 224 is configured so that it can pivot or rotate under control of the absorber controller 802. In this embodiment, a user can identify a particular wavelength of interests to use through a user input 804. The processor 236 then accesses a look up table (LUT) 806 to determine an appropriate angle for the absorber 224 based on the selected wavelength. The processor 236 conveys a signal to the absorber controller 802, which pivots or rotates the absorber 224 based on the angle. In another embodiment, the processor 236 uses Equations 1 and 2 to dynamically calculate the angle on the fly in real time or off line.

Figure 9:
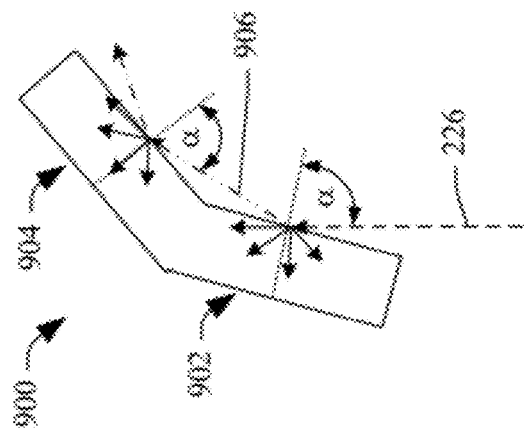
FIG. 9 illustrates an example method.

FIG. 9 schematically illustrates an embodiment that includes an absorber 900 with a first portion 902 that absorbs a substantial amount of the excitation signal 226 traversing the sample carrier 206 as discussed in connection with FIGS. 2 and 3 and a second portion 904 that absorbs a substantial amount of a portion 906 of the excitation signal reflected from the first portion 902 in a similar manner. The absorber 900 may or may not be positional as discussed in connection with FIG. 8. In another embodiment, the absorber 900 includes more than two such portions.

Figure 10:
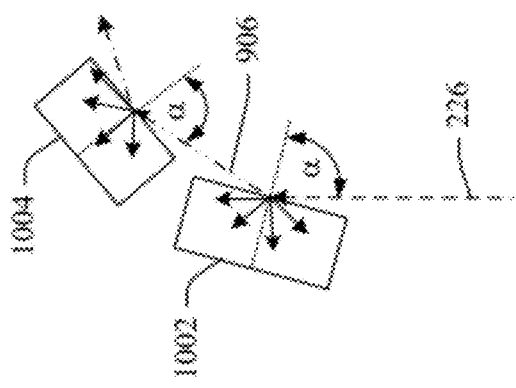

FIG. 10 schematically illustrates an embodiment that includes separate absorbers 1002 and 1004, where the absorber 1002 absorbs a substantial amount of the excitation signal 226 traversing the sample carrier 206 as discussed in connection with FIGS. 2 and 3 and the absorber 1004 absorbs a substantial amount of the portion 906 of the excitation signal reflected from the first portion 902 in a similar manner. In another embodiment, there are more than two absorbers, and one or more of the absorbers are positional as discussed in connection with FIG. 8.

Figure 11:
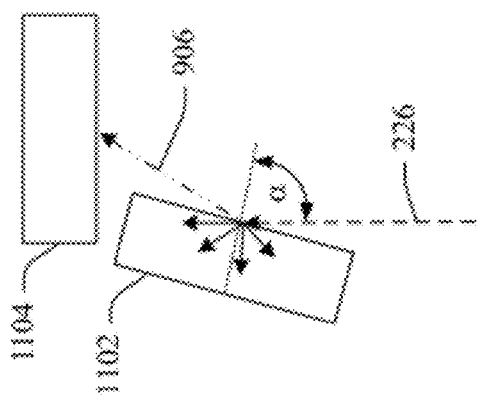

FIG. 11 schematically illustrates an embodiment that includes separate absorbers 1102 and 1104, where the absorber 1102 absorbs a substantial amount of the excitation signal 226 traversing the sample carrier 206 as discussed in connection with FIGS. 2 and 3 and the absorber 1104 absorbs a substantial amount of the portion 906 of the excitation signal reflected from the first portion 902. In this embodiment, the absorber 1102 is substantially similar to the absorber 1002 of FIG. 10, but the absorber 1104 is fixed at a static position, at an angle that may or may not be independent of the wavelength of the excitation signal 104.

Figure 12:
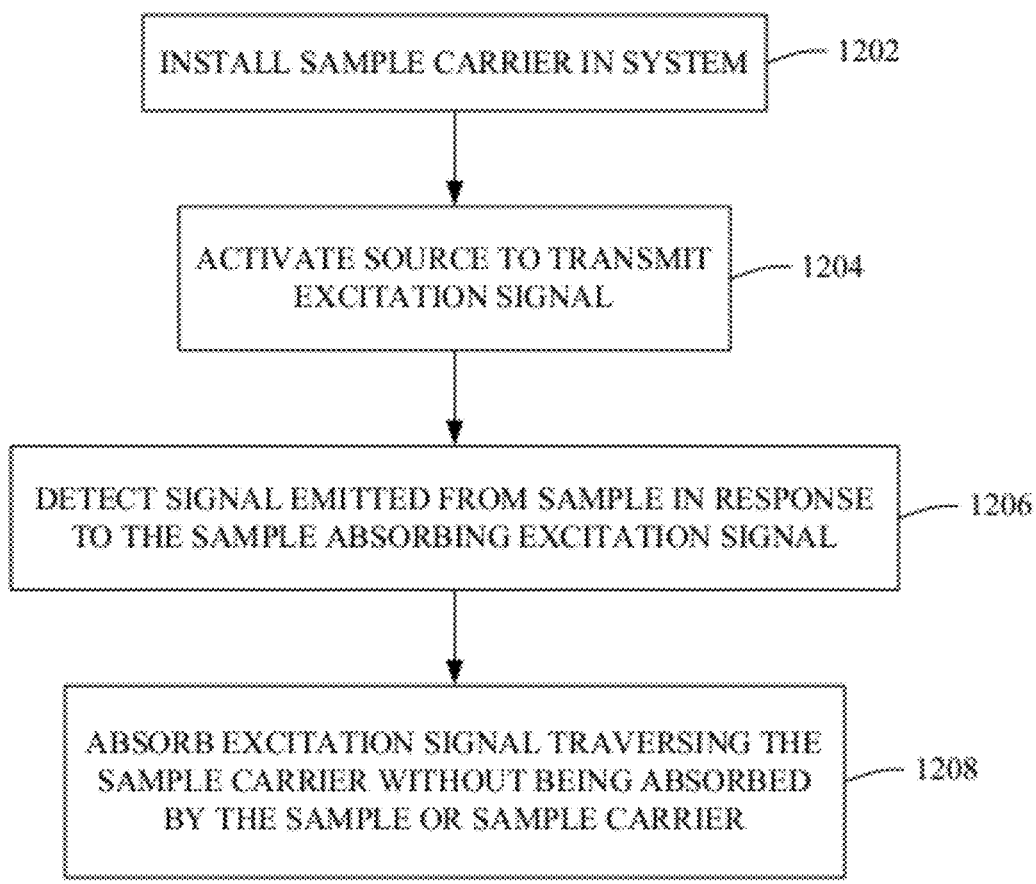

FIG. 12 illustrates an example method in accordance with the optical detection systems discussed herein.

It is to be understood that the following acts are provided for explanatory purposes. In another embodiment, one or more acts can be added and/or one or more acts can be removed. In addition, the order of one or more of the acts can be different. Furthermore, one or more of the acts can occur concurrently.

At 1202, a sample carrier carrying a sample is installed in connection with an optical detection system.

At 1204, a source is activated to transmit an excitation signal.

At 1206, a detector detects a signal emitted by the sample in response to the sample absorbing the excitation signal.

At 1208, an absorber absorbs excitation signal the traverses the sample carrier without being absorbed, as described herein.

The above acts may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention can be construed as including all such modifications and alterations, including insofar as they come within the scope of the appended claims and the equivalents thereof.

What is claimed is:

1. An optical detection system, comprising:
   a sample carrier receiving region that receives a sample carrier carrying a sample;
   a source that emits an excitation signal having a wavelength within a predetermined wavelength range;
   wherein the excitation signal illuminates the sample carrier;
   wherein a first sub-portion of the excitation signal is absorbed by the sample, which emits characteristic radiation in response thereto, and a second sub-portion of the excitation signal traverses the sample carrier;
   a detector that detects the characteristic radiation;
   an absorber that absorbs the excitation signal traversing the sample carrier without being absorbed by the sample or sample carrier, and
   wherein a polarization orientation of the excitation signal is parallel to an incident plane of the absorber.

2. The optical detection system of claim 1, wherein the absorber absorbs at least one of 99% or 95% of the excitation signal traversing the sample carrier.

3. The optical detection system of claim 2, wherein the absorber has a refraction index in a range of 4 to 5.

4. The optical detection system of claim 3, wherein the material includes silicon.

5. The optical detection system of claim 1, wherein the absorber is spatially oriented with respect to a direction of the excitation signal traversing the sample carrier, such that the excitation signal traversing the sample carrier strikes a surface of the absorber an angle that is in a range from 74 and 80 degrees with respect to a normal to the surface, and a polarization orientation of the excitation signal striking the surface is parallel to an incident plane of the absorber.

6. The optical detection system of claim 5, wherein the angle is 77.4 degrees.

7. The optical detection system of claim 5, wherein a reflectance of the surface is less than a half a percent.

8. The optical detection system of claim 5, wherein a reflectance of the surface varies with the angle, and the angle corresponds to an angle at which the reflectance is approximately minimum.

9. The optical detection system of claim 1, wherein the excitation signal has a wavelength of approximately 488 nanometers.

10. The optical detection system of claim 1, wherein the sample includes a DNA fragment labeled with at least one of a plurality of fluorescent dyes, a fluorescent dye absorbs the excitation signal and emits the characteristic radiation, and the characteristic radiation is characteristic of the DNA fragment.

11. The optical detection system of claim 10, further comprising:
   a DNA sequencer that sequences DNA in the sample based on the characteristic radiation of a plurality of DNA fragments.

12. A method, comprising:
   illuminating a sample carrier with an excitation signal, wherein the sample carrier carries a sample, and a first sub-portion of the excitation signal is absorbed by the sample, which emits characteristic radiation in response thereto, and a second sub-portion of the excitation signal traverses the sample carrier;
   detecting, via a detector, the characteristic radiation; and
   absorbing via an absorber the excitation signal traversing the sample carrier,
   wherein a polarization orientation of excitation signal is parallel to an incident plane of the absorber.

13. The method of claim 12, wherein the absorber absorbs at least one of 95% or 99% of the excitation signal traversing the sample carrier.

14. The method of claim 13, wherein the sample includes a DNA fragment and the characteristic radiation is characteristic of the DNA fragment.

15. The method of claim 12, wherein the absorber has a material with a refraction index in a range of 4 to 5.

16. The method of claim 12, wherein absorber includes silicon.

17. The method of claim 16, wherein the absorber is spatially oriented with respect to a direction of the excitation signal traversing the sample carrier such that the excitation signal traversing the sample carrier strikes a surface of the absorber an angle, with respect to a normal to the surface, at which a reflectance of the surface is approximately minimum.

18. The method of claim 17, wherein the angle is approximately 77.4 degrees.

19. The method of claim 12, wherein the excitation signal has a wavelength of approximately 488 nanometers.

20. A device, comprising:
   an optical detection system, including:
      a source that emits an excitation signal that illuminates a sample carrier carrying a plurality of DNA fragments labeled with amino acid specific fluorescent dyes, wherein a first sub-portion of the excitation signal is absorbed by the dyes, which emit characteristic radiation in response thereto, and a second sub-portion of the excitation signal traverses the sample carrier; and
      an absorber that absorbs a portion of the excitation signal that traverses the sample carrier without being absorbed, wherein a polarization orientation of excitation signal is parallel to an incident plane of the absorber.

* * * * *